(12) United States Patent
Sheetz et al.

(10) Patent No.: US 8,801,606 B2
(45) Date of Patent: Aug. 12, 2014

(54) METHOD OF IN VIVO MONITORING USING AN IMAGING SYSTEM INCLUDING SCANNED BEAM IMAGING UNIT

(75) Inventors: Jane A. Sheetz, Cincinnati, OH (US); Jere J. Brophy, Loveland, OH (US); David C. Youmans, Loveland, OH (US); Paul G. Ritchie, Loveland, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 1489 days.

(21) Appl. No.: 11/651,255

(22) Filed: Jan. 9, 2007

(65) Prior Publication Data

US 2008/0167521 A1 Jul. 10, 2008

(51) Int. Cl.
| A61B 1/00 | (2006.01) |
| A61B 1/06 | (2006.01) |
| A61B 1/04 | (2006.01) |
| A61B 1/005 | (2006.01) |
| A61B 1/05 | (2006.01) |
| A61B 5/00 | (2006.01) |
| A61B 5/145 | (2006.01) |

(52) U.S. Cl.
CPC .................. *A61B 1/005* (2013.01); *A61B 1/041* (2013.01); *A61B 1/00172* (2013.01); *A61B 1/00165* (2013.01); *A61B 1/00096* (2013.01); *A61B 1/053* (2013.01); *A61B 5/6882* (2013.01); *A61B 5/14539* (2013.01); *A61B 1/00147* (2013.01); *A61B 1/00101* (2013.01)
USPC ............ 600/160; 600/101; 600/173; 600/182

(58) Field of Classification Search
USPC ......... 600/101, 109, 113, 114, 173, 182, 160, 600/129
See application file for complete search history.

(56) References Cited

U.S. PATENT DOCUMENTS

| 3,758,199 A | 9/1973 | Thaxter |
| 3,959,582 A | 5/1976 | Law et al. |

(Continued)

FOREIGN PATENT DOCUMENTS

| DE | 3837248 | 5/1990 |
| EP | 1139141 | 10/2001 |

(Continued)

OTHER PUBLICATIONS

Ra, H. et al., "Biomedical Optics & Medical Imaging—Microtechnology enables endoscopic confocal microscopy," SPIE (http://spie.org) (2007).

(Continued)

*Primary Examiner* — John P Leubecker

(57) ABSTRACT

A method of monitoring a condition within a patient's body includes locating a scanned beam imaging unit at an imaging location for a period of time to observe and characterize a portion of the patient's anatomy over at least a portion of the period of time. The scanned beam imaging unit is located at the imaging location using a locating instrument. The locating instrument is removed from the patient's body with the scanned beam imaging unit remaining at the imaging location. With the scanned beam imaging unit at the imaging location, a beam of light is scanned across the portion of the anatomy and light is received from the portion of the anatomy. A video image of the portion of the anatomy is produced from imaging data generated using detected light received from the portion of the anatomy.

27 Claims, 11 Drawing Sheets

(56) References Cited

U.S. PATENT DOCUMENTS

| | | | |
|---|---|---|---|
| 3,961,621 A | 6/1976 | Northeved | |
| 4,082,635 A | 4/1978 | Fritz et al. | |
| 4,141,362 A | 2/1979 | Wurster | |
| 4,313,431 A | 2/1982 | Frank | |
| 4,319,563 A | 3/1982 | Kubota | |
| 4,379,039 A | 4/1983 | Fujimoto et al. | |
| 4,403,273 A | 9/1983 | Nishioka | |
| 4,409,477 A | 10/1983 | Carl | |
| 4,421,382 A | 12/1983 | Doi et al. | |
| 4,524,761 A | 6/1985 | Hattori et al. | |
| 4,527,552 A | 7/1985 | Hattori | |
| 4,573,465 A | 3/1986 | Sugiyama et al. | |
| 4,576,999 A | 3/1986 | Eckberg | |
| 4,597,380 A | 7/1986 | Raif et al. | |
| 4,643,967 A | 2/1987 | Bryant | |
| 4,676,231 A | 6/1987 | Hisazumi et al. | |
| 4,760,840 A | 8/1988 | Fournier, Jr. et al. | |
| 4,803,550 A | 2/1989 | Yabe et al. | |
| 4,872,458 A | 10/1989 | Kanehira et al. | |
| 4,902,083 A | 2/1990 | Wells | |
| 4,902,115 A | 2/1990 | Takahashi | |
| 4,934,773 A | 6/1990 | Becker | |
| 4,938,205 A | 7/1990 | Nudelman | |
| 5,003,300 A | 3/1991 | Wells | |
| 5,023,905 A | 6/1991 | Wells et al. | |
| 5,048,077 A | 9/1991 | Wells et al. | |
| 5,074,860 A | 12/1991 | Gregory et al. | |
| 5,078,150 A | 1/1992 | Hara et al. | |
| 5,163,936 A | 11/1992 | Black et al. | |
| 5,163,945 A | 11/1992 | Ortiz et al. | |
| 5,172,685 A | 12/1992 | Nudelman | |
| 5,192,288 A | 3/1993 | Thompson et al. | |
| 5,200,819 A | 4/1993 | Nudelman et al. | |
| 5,200,838 A | 4/1993 | Nudelman et al. | |
| 5,207,670 A | 5/1993 | Sinofsky | |
| 5,218,195 A | 6/1993 | Hakamata | |
| 5,251,025 A | 10/1993 | Cooper et al. | |
| 5,251,613 A | 10/1993 | Adair | |
| 5,269,289 A | 12/1993 | Takehana et al. | |
| 5,318,024 A | 6/1994 | Kittrell et al. | |
| 5,334,991 A | 8/1994 | Wells et al. | |
| 5,368,015 A | 11/1994 | Wilk | |
| 5,370,643 A | 12/1994 | Krivoshlykov et al. | |
| 5,387,197 A | 2/1995 | Smith et al. | |
| 5,393,647 A | 2/1995 | Neukermans et al. | |
| 5,429,604 A | 7/1995 | Hammersmark et al. | |
| 5,436,655 A | 7/1995 | Hiyama et al. | |
| 5,467,104 A | 11/1995 | Furness, III et al. | |
| 5,488,862 A | 2/1996 | Neukermans et al. | |
| 5,531,740 A | 7/1996 | Black | |
| 5,545,211 A | 8/1996 | An et al. | |
| 5,552,452 A | 9/1996 | Khadem et al. | |
| 5,557,444 A | 9/1996 | Melville et al. | |
| 5,590,660 A | 1/1997 | MacAulay et al. | |
| 5,596,339 A | 1/1997 | Furness, III et al. | |
| 5,608,451 A | 3/1997 | Konno et al. | |
| 5,629,790 A | 5/1997 | Neukermans et al. | |
| 5,643,175 A * | 7/1997 | Adair | 600/133 |
| 5,648,618 A | 7/1997 | Neukermans et al. | |
| 5,649,952 A | 7/1997 | Lam | |
| 5,653,677 A * | 8/1997 | Okada et al. | 600/112 |
| 5,657,165 A | 8/1997 | Karpman et al. | |
| 5,658,710 A | 8/1997 | Neukermans | |
| 5,659,327 A | 8/1997 | Furness, III et al. | |
| 5,694,237 A | 12/1997 | Melville | |
| 5,701,132 A | 12/1997 | Kollin et al. | |
| 5,713,891 A | 2/1998 | Poppas | |
| 5,728,121 A | 3/1998 | Bimbo et al. | |
| 5,735,792 A | 4/1998 | Vanden Hoek et al. | |
| 5,742,419 A | 4/1998 | Dickensheets et al. | |
| 5,742,421 A | 4/1998 | Wells et al. | |
| 5,751,465 A | 5/1998 | Melville et al. | |
| 5,768,461 A | 6/1998 | Svetkoff et al. | |
| 5,797,944 A | 8/1998 | Nobles et al. | |
| 5,817,061 A | 10/1998 | Goodwin et al. | |
| 5,823,943 A | 10/1998 | Tomioka et al. | |
| 5,827,176 A | 10/1998 | Tanaka et al. | |
| 5,827,190 A | 10/1998 | Palcic et al. | |
| 5,841,553 A | 11/1998 | Neukermans | |
| 5,861,549 A | 1/1999 | Neukermans et al. | |
| 5,867,297 A | 2/1999 | Kiang et al. | |
| 5,895,866 A | 4/1999 | Neukermans et al. | |
| 5,903,397 A | 5/1999 | Melville et al. | |
| 5,907,425 A | 5/1999 | Dickensheets et al. | |
| 5,913,591 A | 6/1999 | Melville | |
| 5,947,930 A | 9/1999 | Schwemberger et al. | |
| 5,969,465 A | 10/1999 | Neukermans et al. | |
| 5,969,871 A | 10/1999 | Tidwell et al. | |
| 5,982,528 A | 11/1999 | Melville | |
| 5,982,555 A | 11/1999 | Melville et al. | |
| 5,993,037 A | 11/1999 | Tomioka et al. | |
| 5,995,264 A | 11/1999 | Melville | |
| 6,007,208 A | 12/1999 | Dickensheets et al. | |
| 6,008,781 A | 12/1999 | Furness, III et al. | |
| 6,011,889 A | 1/2000 | Daniel et al. | |
| 6,013,025 A | 1/2000 | Bonne et al. | |
| 6,016,440 A | 1/2000 | Simon et al. | |
| 6,017,356 A | 1/2000 | Frederick et al. | |
| 6,017,603 A | 1/2000 | Tokuda et al. | |
| 6,024,744 A | 2/2000 | Kese et al. | |
| 6,043,799 A | 3/2000 | Tidwell | |
| 6,044,705 A | 4/2000 | Neukermans et al. | |
| 6,046,720 A | 4/2000 | Melville et al. | |
| 6,049,407 A | 4/2000 | Melville | |
| 6,056,721 A | 5/2000 | Shulze et al. | |
| 6,057,952 A | 5/2000 | Kubo et al. | |
| 6,059,720 A | 5/2000 | Furusawa et al. | |
| 6,061,163 A | 5/2000 | Melville | |
| 6,064,779 A | 5/2000 | Neukermans et al. | |
| 6,069,725 A | 5/2000 | Melville | |
| 6,086,528 A | 7/2000 | Adair | |
| 6,086,531 A | 7/2000 | Tomioka et al. | |
| 6,088,145 A | 7/2000 | Dickensheets et al. | |
| 6,097,353 A | 8/2000 | Melville et al. | |
| 6,122,394 A | 9/2000 | Neukermans et al. | |
| 6,139,175 A | 10/2000 | Tomioka et al. | |
| 6,140,979 A | 10/2000 | Gerhard et al. | |
| 6,151,167 A | 11/2000 | Melville | |
| 6,154,305 A | 11/2000 | Dickensheets et al. | |
| 6,154,321 A | 11/2000 | Melville et al. | |
| 6,157,352 A | 12/2000 | Kollin et al. | |
| 6,166,841 A | 12/2000 | Melville | |
| 6,172,789 B1 | 1/2001 | Kino et al. | |
| 6,178,346 B1 | 1/2001 | Amundson et al. | |
| 6,179,776 B1 | 1/2001 | Adams et al. | |
| 6,191,761 B1 | 2/2001 | Melville et al. | |
| 6,192,267 B1 | 2/2001 | Scherninski et al. | |
| 6,200,595 B1 | 3/2001 | Motoyashiki et al. | |
| 6,204,829 B1 | 3/2001 | Tidwell | |
| 6,204,832 B1 | 3/2001 | Melville et al. | |
| 6,207,392 B1 | 3/2001 | Weiss et al. | |
| 6,210,401 B1 | 4/2001 | Lai | |
| 6,220,711 B1 | 4/2001 | Melville | |
| 6,221,068 B1 | 4/2001 | Fried et al. | |
| 6,229,139 B1 | 5/2001 | Neukermans et al. | |
| 6,235,017 B1 | 5/2001 | Jegorov et al. | |
| 6,243,186 B1 | 6/2001 | Melville | |
| 6,245,590 B1 | 6/2001 | Wine et al. | |
| 6,256,131 B1 | 7/2001 | Wine et al. | |
| 6,257,727 B1 | 7/2001 | Melville | |
| 6,272,907 B1 | 8/2001 | Neukermans et al. | |
| 6,276,798 B1 | 8/2001 | Gil et al. | |
| 6,281,862 B1 | 8/2001 | Tidwell et al. | |
| 6,284,185 B1 | 9/2001 | Tokuda et al. | |
| 6,285,489 B1 | 9/2001 | Helsel et al. | |
| 6,285,505 B1 | 9/2001 | Melville et al. | |
| 6,288,816 B1 | 9/2001 | Melville et al. | |
| 6,292,287 B1 | 9/2001 | Fujinoki | |
| 6,293,911 B1 | 9/2001 | Imaizumi et al. | |
| 6,294,239 B1 | 9/2001 | Tokuda et al. | |
| 6,294,775 B1 | 9/2001 | Seibel et al. | |
| 6,296,608 B1 | 10/2001 | Daniels et al. | |
| 6,317,103 B1 | 11/2001 | Furness, III et al. | |
| 6,323,037 B1 | 11/2001 | Lauto et al. | |

(56) References Cited

U.S. PATENT DOCUMENTS

| | | |
|---|---|---|
| 6,324,007 B1 | 11/2001 | Melville |
| 6,327,493 B1 | 12/2001 | Ozawa et al. |
| 6,331,909 B1 | 12/2001 | Dunfield |
| 6,333,110 B1 | 12/2001 | Barbera-Guillem |
| 6,338,641 B2 | 1/2002 | Nicholls |
| 6,352,344 B2 | 3/2002 | Tidwell |
| 6,353,183 B1 | 3/2002 | Ott et al. |
| 6,362,912 B1 | 3/2002 | Lewis et al. |
| 6,364,829 B1 | 4/2002 | Fulghum |
| 6,366,726 B1 | 4/2002 | Wach et al. |
| 6,369,928 B1 | 4/2002 | Mandella et al. |
| 6,369,953 B2 | 4/2002 | Melville et al. |
| 6,369,954 B1 | 4/2002 | Berge et al. |
| 6,370,406 B1 | 4/2002 | Wach et al. |
| 6,370,422 B1 | 4/2002 | Richards-Kortum et al. |
| 6,373,995 B1 | 4/2002 | Moore |
| 6,384,406 B1 | 5/2002 | Wine et al. |
| 6,388,641 B2 | 5/2002 | Tidwell et al. |
| 6,392,220 B1 | 5/2002 | Slater et al. |
| 6,396,461 B1 | 5/2002 | Lewis et al. |
| 6,414,779 B1 | 7/2002 | Mandella et al. |
| 6,417,502 B1 | 7/2002 | Stoner et al. |
| 6,423,956 B1 | 7/2002 | Mandella et al. |
| 6,425,900 B1 | 7/2002 | Knodel et al. |
| 6,426,013 B1 | 7/2002 | Neukermans et al. |
| 6,433,907 B1 | 8/2002 | Lippert et al. |
| 6,435,637 B1 | 8/2002 | Lyman |
| 6,441,356 B1 | 8/2002 | Mandella et al. |
| 6,445,362 B1 | 9/2002 | Tegreene |
| 6,447,524 B1 | 9/2002 | Knodel et al. |
| 6,462,770 B1 | 10/2002 | Cline et al. |
| 6,464,363 B1 | 10/2002 | Nishioka et al. |
| 6,467,345 B1 | 10/2002 | Neukermans et al. |
| 6,470,124 B1 | 10/2002 | Le Gargasson et al. |
| 6,477,403 B1 | 11/2002 | Eguchi et al. |
| 6,478,809 B1 | 11/2002 | Brotz |
| 6,485,413 B1 | 11/2002 | Boppart et al. |
| 6,492,962 B2 | 12/2002 | Melville et al. |
| 6,494,578 B1 | 12/2002 | Plummer et al. |
| 6,503,196 B1 | 1/2003 | Kehr et al. |
| 6,510,338 B1 | 1/2003 | Irion et al. |
| 6,512,622 B2 | 1/2003 | Wine et al. |
| 6,513,939 B1 | 2/2003 | Fettig et al. |
| 6,515,278 B2 | 2/2003 | Wine et al. |
| 6,515,781 B2 | 2/2003 | Lewis et al. |
| 6,520,972 B2 | 2/2003 | Peters |
| 6,522,444 B2 | 2/2003 | Mandella et al. |
| 6,525,310 B2 | 2/2003 | Dunfield |
| 6,527,708 B1 | 3/2003 | Nakamura et al. |
| 6,529,770 B1 | 3/2003 | Grimblatov |
| 6,530,698 B1 | 3/2003 | Kuhara et al. |
| 6,535,183 B2 | 3/2003 | Melville et al. |
| 6,535,325 B2 | 3/2003 | Helsel et al. |
| 6,537,211 B1 | 3/2003 | Wang et al. |
| 6,538,625 B2 | 3/2003 | Tidwell et al. |
| 6,545,260 B1 | 4/2003 | Katashiro et al. |
| 6,560,028 B2 | 5/2003 | Melville et al. |
| 6,563,105 B2 | 5/2003 | Seibel et al. |
| 6,563,106 B1 | 5/2003 | Bowers et al. |
| 6,572,606 B2 | 6/2003 | Kliewer et al. |
| 6,583,117 B2 | 6/2003 | Owen et al. |
| 6,583,772 B1 | 6/2003 | Lewis et al. |
| 6,585,642 B2 | 7/2003 | Christopher |
| 6,603,552 B1 | 8/2003 | Cline et al. |
| 6,608,297 B2 | 8/2003 | Neukermans et al. |
| 6,632,171 B2 * | 10/2003 | Iddan et al. .................. 600/106 |
| 6,639,570 B2 | 10/2003 | Furness, III et al. |
| 6,639,719 B2 | 10/2003 | Tegreene et al. |
| 6,650,877 B1 | 11/2003 | Tarbouriech et al. |
| 6,653,621 B2 | 11/2003 | Wine et al. |
| 6,654,158 B2 | 11/2003 | Helsel et al. |
| 6,661,393 B2 | 12/2003 | Tegreene et al. |
| 6,674,993 B1 | 1/2004 | Tarbouriech |
| 6,685,804 B1 | 2/2004 | Ikeda et al. |
| 6,687,034 B2 | 2/2004 | Wine et al. |
| 6,689,056 B1 * | 2/2004 | Kilcoyne et al. .............. 600/300 |
| 6,699,170 B1 | 3/2004 | Crocker et al. |
| 6,700,552 B2 | 3/2004 | Kollin et al. |
| 6,714,331 B2 | 3/2004 | Lewis et al. |
| 6,734,835 B2 | 5/2004 | Tidwell et al. |
| 6,736,511 B2 | 5/2004 | Plummer et al. |
| 6,741,884 B1 | 5/2004 | Freeman et al. |
| 6,749,346 B1 | 6/2004 | Dickensheets et al. |
| 6,755,536 B2 | 6/2004 | Tegreene et al. |
| 6,762,867 B2 | 7/2004 | Lippert et al. |
| 6,768,588 B2 | 7/2004 | Urey |
| 6,771,001 B2 | 8/2004 | Mao et al. |
| 6,782,748 B2 | 8/2004 | Weber et al. |
| 6,786,382 B1 | 9/2004 | Hoffman |
| 6,790,173 B2 | 9/2004 | Saadat et al. |
| 6,795,221 B1 | 9/2004 | Urey |
| 6,802,809 B2 | 10/2004 | Okada |
| 6,803,561 B2 | 10/2004 | Dunfield |
| 6,814,699 B2 | 11/2004 | Ross et al. |
| 6,821,245 B2 | 11/2004 | Cline et al. |
| 6,845,190 B1 | 1/2005 | Smithwick et al. |
| 6,856,436 B2 | 2/2005 | Brukilacchio et al. |
| 6,856,712 B2 | 2/2005 | Fauver et al. |
| 6,879,428 B2 | 4/2005 | Massieu |
| 6,888,552 B2 | 5/2005 | Debevec et al. |
| 6,894,823 B2 | 5/2005 | Taylor et al. |
| 6,899,675 B2 | 5/2005 | Cline et al. |
| 6,902,527 B1 | 6/2005 | Doguchi et al. |
| 6,905,057 B2 | 6/2005 | Swayze et al. |
| 6,939,364 B1 | 9/2005 | Soltz et al. |
| 6,957,898 B2 | 10/2005 | Yu |
| 6,967,757 B1 | 11/2005 | Allen et al. |
| 6,974,472 B2 | 12/2005 | Hong et al. |
| 6,975,898 B2 | 12/2005 | Seibel et al. |
| 6,976,994 B2 | 12/2005 | Ballou et al. |
| 6,978,921 B2 | 12/2005 | Shelton, IV et al. |
| 6,985,271 B2 | 1/2006 | Yazdi et al. |
| 6,991,602 B2 | 1/2006 | Nakazawa et al. |
| 7,005,195 B2 | 2/2006 | Cheng et al. |
| 7,009,634 B2 | 3/2006 | Iddan et al. |
| 7,013,730 B2 | 3/2006 | Malametz |
| 7,015,956 B2 | 3/2006 | Luo et al. |
| 7,018,401 B1 | 3/2006 | Hyodoh et al. |
| 7,023,402 B2 | 4/2006 | Lewis et al. |
| 7,025,777 B2 | 4/2006 | Moore |
| 7,033,348 B2 | 4/2006 | Alfano et al. |
| 7,035,777 B2 | 4/2006 | Araki et al. |
| 7,061,450 B2 | 6/2006 | Bright et al. |
| 7,065,301 B2 | 6/2006 | Shastri et al. |
| 7,066,879 B2 | 6/2006 | Fowler et al. |
| 7,071,594 B1 | 7/2006 | Yan et al. |
| 7,071,931 B2 | 7/2006 | Tegreene et al. |
| 7,078,378 B1 | 7/2006 | Owen et al. |
| 7,108,656 B2 | 9/2006 | Fujikawa et al. |
| 7,112,302 B2 | 9/2006 | Yoshimi et al. |
| 7,126,903 B2 | 10/2006 | Feenstra et al. |
| 7,189,961 B2 | 3/2007 | Johnston et al. |
| 7,190,329 B2 | 3/2007 | Lewis et al. |
| 7,232,071 B2 | 6/2007 | Lewis et al. |
| 7,242,833 B2 | 7/2007 | Yang et al. |
| 7,271,383 B2 | 9/2007 | Chee |
| 7,391,013 B2 | 6/2008 | Johnston et al. |
| 7,530,948 B2 * | 5/2009 | Seibel et al. .................. 600/178 |
| 7,727,145 B2 * | 6/2010 | Yokoi et al. .................. 600/109 |
| 2001/0012429 A1 | 8/2001 | Wach et al. |
| 2001/0055462 A1 | 12/2001 | Seibel |
| 2002/0015724 A1 | 2/2002 | Yang et al. |
| 2002/0024495 A1 | 2/2002 | Lippert et al. |
| 2002/0050956 A1 | 5/2002 | Gerhard et al. |
| 2002/0075284 A1 | 6/2002 | Rabb, III |
| 2002/0088925 A1 | 7/2002 | Nestorovic et al. |
| 2002/0115922 A1 | 8/2002 | Waner et al. |
| 2002/0141026 A1 | 10/2002 | Wiklof et al. |
| 2002/0158814 A1 | 10/2002 | Bright et al. |
| 2002/0163484 A1 | 11/2002 | Furness, III et al. |
| 2002/0167462 A1 | 11/2002 | Lewis et al. |
| 2002/0171776 A1 | 11/2002 | Tegreene et al. |
| 2002/0171937 A1 | 11/2002 | Tegreene et al. |
| 2003/0016187 A1 | 1/2003 | Melville et al. |

(56) References Cited

U.S. PATENT DOCUMENTS

| | | |
|---|---|---|
| 2003/0030753 A1 | 2/2003 | Kondo et al. |
| 2003/0032143 A1 | 2/2003 | Neff et al. |
| 2003/0034709 A1 | 2/2003 | Jerman |
| 2003/0058190 A1 | 3/2003 | Lewis et al. |
| 2003/0086172 A1 | 5/2003 | Urey |
| 2003/0092995 A1 | 5/2003 | Thompson |
| 2003/0130562 A1 | 7/2003 | Barbato et al. |
| 2003/0142934 A1 | 7/2003 | Pan et al. |
| 2003/0159447 A1 | 8/2003 | Sergio et al. |
| 2003/0208107 A1 | 11/2003 | Rafael |
| 2003/0214460 A1 | 11/2003 | Kovacs |
| 2003/0216729 A1 | 11/2003 | Marchitto et al. |
| 2004/0004585 A1 | 1/2004 | Brown et al. |
| 2004/0057103 A1 | 3/2004 | Bernstein |
| 2004/0075624 A1 | 4/2004 | Tegreene et al. |
| 2004/0076390 A1 | 4/2004 | Dong Yang et al. |
| 2004/0085261 A1 | 5/2004 | Lewis et al. |
| 2004/0085617 A1 | 5/2004 | Helsel et al. |
| 2004/0087844 A1 | 5/2004 | Yen |
| 2004/0101822 A1 | 5/2004 | Wiesner et al. |
| 2004/0113059 A1 | 6/2004 | Kawano et al. |
| 2004/0118821 A1 | 6/2004 | Han et al. |
| 2004/0119004 A1 | 6/2004 | Wine et al. |
| 2004/0122328 A1 | 6/2004 | Wang et al. |
| 2004/0133786 A1 | 7/2004 | Tarbouriech |
| 2004/0151466 A1 | 8/2004 | Crossman-Bosworth et al. |
| 2004/0155186 A1 | 8/2004 | Nestorovic et al. |
| 2004/0155834 A1 | 8/2004 | Wit et al. |
| 2004/0179254 A1 | 9/2004 | Lewis et al. |
| 2004/0196518 A1 | 10/2004 | Wine et al. |
| 2004/0223202 A1 | 11/2004 | Lippert et al. |
| 2004/0225222 A1 | 11/2004 | Zeng et al. |
| 2004/0236371 A1 | 11/2004 | McNally-Heintzelman et al. |
| 2004/0240866 A1 | 12/2004 | Ramsbottom |
| 2004/0252377 A1 | 12/2004 | Urey |
| 2004/0254474 A1 | 12/2004 | Seibel et al. |
| 2005/0010787 A1 | 1/2005 | Tarbouriech |
| 2005/0014995 A1 | 1/2005 | Amundson et al. |
| 2005/0020877 A1 | 1/2005 | Ishihara et al. |
| 2005/0020926 A1 | 1/2005 | Wiklof et al. |
| 2005/0023356 A1 | 2/2005 | Wiklof et al. |
| 2005/0030305 A1 | 2/2005 | Brown et al. |
| 2005/0038322 A1 | 2/2005 | Banik |
| 2005/0116038 A1* | 6/2005 | Lewis et al. .............. 235/454 |
| 2005/0162762 A1 | 7/2005 | Novak |
| 2005/0165272 A1* | 7/2005 | Okada et al. ............... 600/114 |
| 2005/0187441 A1 | 8/2005 | Kawasaki et al. |
| 2005/0203343 A1 | 9/2005 | Kang et al. |
| 2005/0215911 A1* | 9/2005 | Alfano et al. .............. 600/476 |
| 2005/0240147 A1 | 10/2005 | Makower et al. |
| 2005/0288555 A1 | 12/2005 | Binmoeller |
| 2006/0010985 A1 | 1/2006 | Schneider |
| 2006/0084867 A1 | 4/2006 | Tremblay et al. |
| 2006/0122522 A1* | 6/2006 | Chavan et al. ............. 600/505 |
| 2006/0164330 A1 | 7/2006 | Bright et al. |
| 2006/0183246 A1 | 8/2006 | Wiesner et al. |
| 2006/0195014 A1 | 8/2006 | Seibel et al. |
| 2006/0238774 A1 | 10/2006 | Lindner et al. |
| 2006/0245971 A1 | 11/2006 | Burns et al. |
| 2006/0284790 A1 | 12/2006 | Tegreene et al. |
| 2007/0032701 A1* | 2/2007 | Fowler et al. .............. 600/173 |
| 2007/0038119 A1 | 2/2007 | Chen et al. |
| 2007/0046778 A1 | 3/2007 | Ishihara et al. |
| 2007/0135770 A1 | 6/2007 | Hunt et al. |
| 2007/0142714 A1 | 6/2007 | Shumate et al. |
| 2007/0156021 A1 | 7/2007 | Morse et al. |
| 2007/0161876 A1 | 7/2007 | Bambot et al. |
| 2007/0162093 A1 | 7/2007 | Porter et al. |
| 2007/0167681 A1 | 7/2007 | Gill et al. |
| 2007/0173686 A1* | 7/2007 | Lin et al. .................. 600/102 |
| 2007/0173707 A1 | 7/2007 | Mitra |
| 2007/0179366 A1 | 8/2007 | Pewzner et al. |
| 2007/0197865 A1* | 8/2007 | Miyake et al. ............. 600/109 |
| 2007/0197874 A1 | 8/2007 | Ishihara |
| 2007/0197875 A1 | 8/2007 | Osaka |
| 2007/0203413 A1 | 8/2007 | Frangioni |
| 2007/0213588 A1 | 9/2007 | Morishita et al. |
| 2007/0213618 A1 | 9/2007 | Li et al. |
| 2007/0225695 A1 | 9/2007 | Mayer et al. |
| 2007/0238930 A1 | 10/2007 | Wiklof et al. |
| 2007/0244365 A1 | 10/2007 | Wiklof |
| 2007/0260121 A1 | 11/2007 | Bakos et al. |
| 2007/0260273 A1 | 11/2007 | Cropper et al. |
| 2008/0013960 A1 | 1/2008 | Tearney et al. |
| 2008/0058629 A1 | 3/2008 | Seibel et al. |
| 2009/0005636 A1* | 1/2009 | Pang et al. .............. 600/102 |
| 2009/0182202 A1 | 7/2009 | Vayser et al. |
| 2010/0056864 A1 | 3/2010 | Lee |

FOREIGN PATENT DOCUMENTS

| | | |
|---|---|---|
| EP | 1716802 | 11/2006 |
| EP | 1747751 | 1/2007 |
| EP | 1797813 | 6/2007 |
| JP | 2007-244590 | 9/2007 |
| JP | 2007-244680 | 9/2007 |
| WO | WO 98/13720 | 4/1998 |
| WO | WO 99/18456 | 4/1999 |
| WO | 99/58930 | 11/1999 |
| WO | 00/13210 | 3/2000 |
| WO | 01/10322 | 2/2001 |
| WO | 01/60274 | 8/2001 |
| WO | 02/062239 | 8/2002 |
| WO | WO 03/069380 | 8/2003 |
| WO | 03/088643 | 10/2003 |
| WO | 03/098918 | 11/2003 |
| WO | 03/101287 | 11/2003 |
| WO | 2006/020605 | 2/2006 |
| WO | WO 2006/049787 | 5/2006 |
| WO | WO 2006/055733 | 5/2006 |
| WO | 2007/041542 | 4/2007 |
| WO | 2007/070831 | 6/2007 |
| WO | WO 2007/067163 | 6/2007 |
| WO | WO 2007/084915 | 7/2007 |

OTHER PUBLICATIONS

PCT, International Search Report, PCT/US2008/066552 (Oct. 23, 2008).

Kiang, M-H et al., "Surface-Micromachined Electrostatic-Comb Driven Scanning Micromirrors for Barcode Scanners" (date of first publication unknown).

Lewis, J.R. et al., "Scanned beam medical imager," MOEMS Display and Imaging Systems II, Proceedings of SPIE vol. 5348, pp. 40-51 (2004).

James, R. et al., "Update on MEMS-based Scanned Beam Imager" (date of first publication unknown).

Wiklof, C., "Display technology spawns laser camera," Laser Focus World (Dec. 2004).

"Press Information—Phillips' Fluid Lenses Bring Things into Focus," http://www.newscenter.philips.com (Mar. 3, 2004).

Lettice, J., "The $5 'no moving parts' fluid zoom lens—twice," The Register (Mar. 15, 2004).

"Volcano Products—IVUS Imaging Visions® PV018," http://www.volcanotherapeutics.com (date of first publication unknown).

Barhoum, E.S. et al., "Optical modeling of an ultrathin scanning fiber endoscope, a preliminary study of confocal versus non-confocal detection," Optics Express, vol. 13, No. 19, pp. 7548-7652 (Sep. 19, 2005).

"Crystalplex Technology—PlxBead™ Superior Qualities," http:www.crystalplex.com (date of first publication unknown).

"Microvision [illuminating information] Products/Overview, Corporate Overview Presentation 2006" (2006).

"Holographic Beam Combiner for Ladar, Printer, Fiber Optics, and Cancer Treatment," by Digital Optics Technologies, Inc., http://www.mdatechnology.net (date of first publication unknown).

Brown, D.M., Abstract from SPIE Digital Library for "High-power laser diode beam combiner," Optical Engineering, vol. 42, Issue 11 (2003).

Literature entitled "All fiber beam combiner from Point Source" (Oct. 13, 2006).

(56) References Cited

OTHER PUBLICATIONS

"Custom Polarzing Cube Beamsplitters," from GlobalSpec the Engineering Search Engine, http://www.globalspec.com (date of first publication unknown).
Literature entitled "Dallas Semiconductor Maxim—Visible-Laser Driver has Digitally Controlled Power Modulation," by Maxim Integrated Products, http://www.maxim-ic.com (Jul. 1, 2001).
"Scan Mode Strategies for SCUBA-2" (May 25, 2005).
Seifert, M. et al., "High Power Diode Laser Beam Scanning in Multi-Kilowatt Range," Proceedings of the 23rd International Congress on Applications of Lasers and Electro-Optics (2004).
Jutzi, B. et al., "Sub-Pixel Edge Localization Based on Laser Waveform Analysis," ISPRS WG III/3, III/4, V/3 Workshop "Laser scanning 2005," Enschede, the Netherlands (Sep. 12-14, 2005).
"Bladeless Trocars," by Johnson & Johnson, http://www.jnjgateway.com (date of first publication unknown).
Yeh, R. et al., "Microelectromechanical Components for Articulated Microrobots" (date of first publication unknown).
Xu, Q. et al., "Micrometre-scale silicon electro-optic modulator," Nature, vol. 435, pp. 325-327 (May 19, 2005).
Park, H. et al., "Development of Double-Sided Silicon Strip Position Sensor," 2005 IEEE Nuclear Science Symposium Conference Record, pp. 781-785 (2005).
Hammond, S.W., "Architecture and Operation of a Systolic Sparse Matrix Engine," Proceedings of the 3rd SIAM Conference on Parallel Processing for Scientific Computing, pp. 419-423 (1987).
PCT, International Search Report, PCT/US2008/056589 (Jul. 30, 2008).
PCT, International Search Report, PCT/US2008/059231 (Jul. 4, 2008).
PCT, International Search Report, PCT/US2007/087923 (May 21, 2008).
PCT, International Search Report, PCT/US2008/056596 (Jun. 23, 2008).
PCT, International Search Report, PCT/US2008/059235 (Jul. 14, 2008).
PCT, International Search Report, PCT/US2007/087930 (Jul. 3, 2008).
PCT, International Search Report, PCT/US2008/051274 (Jul. 18, 2008).
International Search Report issued regarding International Application No. PCT/US2007/078868 (Mar. 28, 2008).
US, Office Action, U.S. Appl. No. 11/749,188 (Jan. 4, 2011).
US, Office Action, U.S. Appl. No. 11/749,188 (Aug. 19, 2011).
US, Advisory Action, U.S. Appl. No. 11/749,188 (Nov. 14, 2011).
US, Notice of Allowance, U.S. Appl. No. 11/749,188 (May 24, 2012).

* cited by examiner

METHOD OF IN VIVO MONITORING USING AN IMAGING SYSTEM INCLUDING SCANNED BEAM IMAGING UNIT

FIELD OF THE INVENTION

The present application relates generally to visualization systems and more particularly to a method of in vivo monitoring using an imaging system including a scanned beam imaging unit.

BACKGROUND

Imaging systems are frequently employed to provide an image of a site within a patient's body. For example, endoscopes may be used that include a camera or other imaging device that can provide an image prior to or during a minimally invasive diagnostic or surgical medical procedure. The camera typically includes a solid state image sensor such as a CCD array. After the medical procedure is completed, the endoscope including camera is removed from the patient's body.

Another existing imaging system is a pill camera. Pill cameras are frequently employed for providing snapshots of the small intestine, for example, that cannot be reached by a colonoscope. Pill cameras are typically swallowed and move through the digestive tract by peristalsis.

SUMMARY

In an aspect, a method of monitoring a condition within a patient's body includes locating a scanned beam imaging unit at an imaging location for a period of time to observe and characterize a portion of the patient's anatomy over at least a portion of the period of time. The scanned beam imaging unit is located at the imaging location using a locating instrument. The locating instrument is removed from the patient's body with the scanned beam imaging unit remaining at the imaging location. With the scanned beam imaging unit at the imaging location, a beam of light is scanned across the portion of the anatomy and light is received from the portion of the anatomy. A video image of the portion of the anatomy is produced from imaging data generated using detected light received from the portion of the anatomy.

In another aspect, an imaging system for monitoring a condition within a patient's body includes a scanned beam imaging unit comprising a reflector that directs a beam of light across a portion of the patient's anatomy and a portable control unit linked to the scanned beam imaging unit. The portable control unit includes a power source, a light source that generates the beam of light and a memory for saving imaging data generated using the scanned beam imaging unit.

In another aspect, a method of monitoring a condition within a patient's body includes locating a scanned beam imaging unit at an imaging location for a period of time to observe and characterize a portion of the patient's anatomy over at least a portion of the period of time. A portable control unit is provided that is in communication with the scanned beam imaging unit with the scanned beam imaging unit located at the imaging location. The portable control unit includes a recording medium for saving imaging data generated using the scanned beam imaging unit for producing a video image of the portion of the patient's anatomy.

In another aspect, an imaging system for monitoring a condition within a patient's body includes a control unit including a light source that generates a beam of light and a memory for saving imaging data. A scanned beam imaging unit is capable of communicating with the control unit. The scanned beam imaging unit includes a reflector that receives the beam of light from the light source and scans the beam of light across a portion of the patient's anatomy. Connecting structure is configured to affix the scanned beam imaging unit at an imaging location for scanning the beam of light across the portion of the patient's anatomy over a period of time.

The details of one or more embodiments of the invention are set forth in the accompanying drawings and the description below. Other features, objects, and advantages of the invention will be apparent from the description and the drawings, and from the claims.

DETAILED DESCRIPTION

Figure 1:
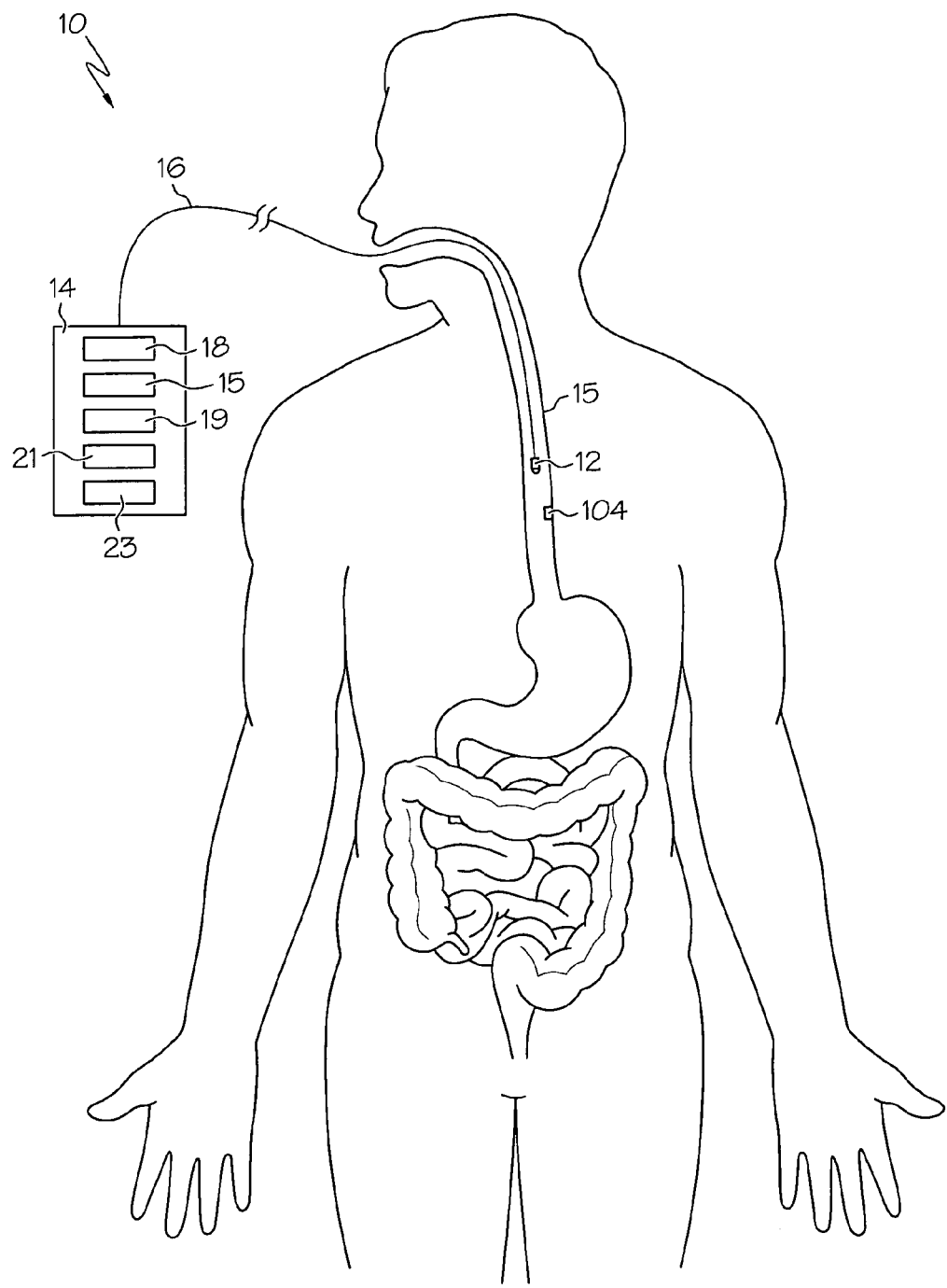
FIG. 1 is a diagrammatic view of an embodiment of an imaging system within a patient's body.

Referring to FIG. 1, an imaging system 10 for generating and recording imaging data includes a scanned beam imaging unit 12 that is connected to a control unit 14 by a line 16. Control unit 14 may include a power source 15 (e.g., batteries), a light source 18 (e.g., light emitting diodes (LEDs), lasers, etc.), a receiver 21, a digitizer 23 and a recording medium 19 (e.g., memory). The scanned beam imaging unit 12 is shown as free hanging within the esophagus 15 as an illustrative example for imaging a region of the esophagus, however, the scanned beam imaging unit 12 may be used to visualize other anatomical structures such as other regions of the gastrointestinal tract (e.g., stomach, duodenum, small intestine, colon), the respiratory tract (e.g., nose, lower respiratory tract), the urinary tract, the female reproductive system (e.g., cervix, uterus, Fallopian tubes), normally closed body cavities (e.g., abdominal or pelvic cavity, interior of a joint, organs of the chest), during pregnancy (e.g., amnion, fetus), blood vessels, peritoneal space external to organ structures, etc. In some embodiments, the scanned beam imaging unit 12 may be introduced into the body through an incision, needle or other artificial opening in the body.

Figure 2:
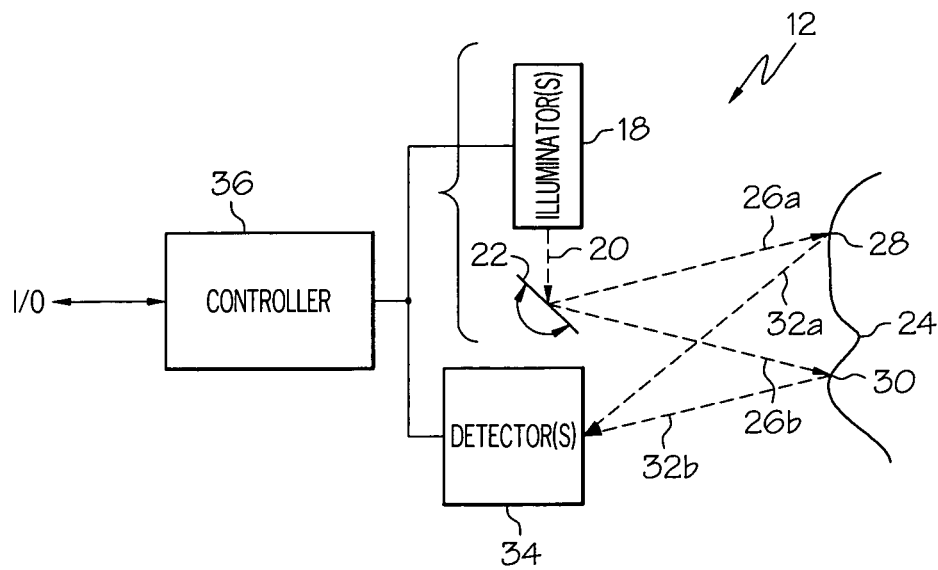
FIG. 2 is a diagrammatic view of the imaging system of FIG. 1.

Referring to FIG. 2, scanned beam imaging unit 12 receives a first beam of light 20 from the light source 18 (e.g., through an optical fiber, such as a single mode fiber). A reflector 22 deflects the first beam of light 20 across a field of view 24 (e.g., the portion of the anatomy to be visualized) to produce a second scanned beam of light 26. The scanned beam of light 26 sequentially illuminates areas 28 and 30 in the field of view 24. While the scanned beam of light 20 illuminates the areas 28 and 30, the scanned beam of light is reflected, absorbed, scattered, refracted or otherwise affected by the properties of the of the object or material to produce reflected light energy. A portion of the light energy 32 travels to one or more detectors 34 (e.g., via a light collection system) that receive the light and produce electrical signals corresponding to the amount of light energy received. The electrical signals drive a controller 36 that is used to build up a digital image and transmits it for further processing, decoding, archiving, printing, display or other treatment or use.

Light source 18 may include multiple emitters of various wavelengths such as LEDs, lasers, thermal sources, arc sources, fluorescent sources, gas discharge sources, etc. Light source 18 may also include beam shaping optics such as one or more collimating lenses and/or apertures. Light beam 20 may include a plurality of beams converging onto a single reflector 22 or onto separate reflectors.

Some embodiments use a micro-electromechanical (MEM) reflector. MEM reflectors are described in, for example, U.S. Pat. No. 6,140,979, entitled SCANNED DISPLAY WITH PINCH, TIMING, AND DISTORTION CORRECTION; U.S. Pat. No. 6,245,590, entitled FREQUENCY TUNABLE RESONANT SCANNER AND METHOD OF MAKING; U.S. Pat. No. 6,285,489, entitled FREQUENCY TUNABLE RESONANT SCANNER WITH AUXILIARY ARMS; U.S. Pat. No. 6,331,909, entitled FREQUENCY TUNABLE RESONANT SCANNER; U.S. Pat. No. 6,362,912, entitled SCANNED IMAGING APPARATUS WITH SWITCHED FEEDS; U.S. Pat. No. 6,384,406, entitled ACTIVE TUNING OF A TORSIONAL RESONANT STRUCTURE; U.S. Pat. No. 6,433,907, entitled SCANNED DISPLAY WITH PLURALITY OF SCANNING ASSEMBLIES; U.S. Pat. No. 6,512,622, entitled ACTIVE TUNING OF A TORSIONAL RESONANT STRUCTURE; U.S. Pat. No. 6,515,278, entitled FREQUENCY TUNABLE RESONANT SCANNER AND METHOD OF MAKING; U.S. Pat. No. 6,515,781, entitled SCANNED IMAGING APPARATUS WITH SWITCHED FEEDS; U.S. Pat. No. 6,525,310, entitled FREQUENCY TUNABLE RESONANT SCANNER; and U.S. patent application Ser. No. 10/873,540, entitled SCANNING ENDOSCOPE; all of which are hereby incorporated by reference in their entirety as if fully set forth herein.

Figure 3:
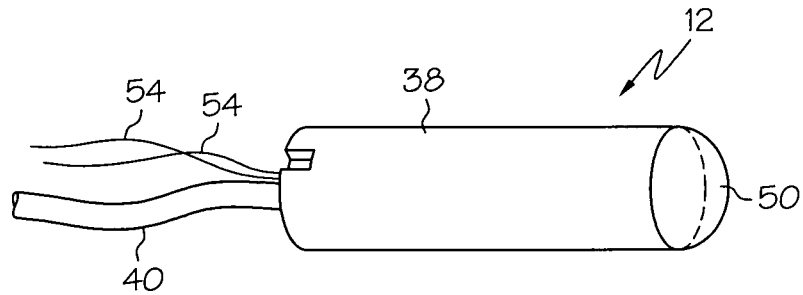
FIG. 3 is a perspective view of an embodiment of a scanned beam imaging unit for use in the imaging system of FIG. 1.
Figure 4:
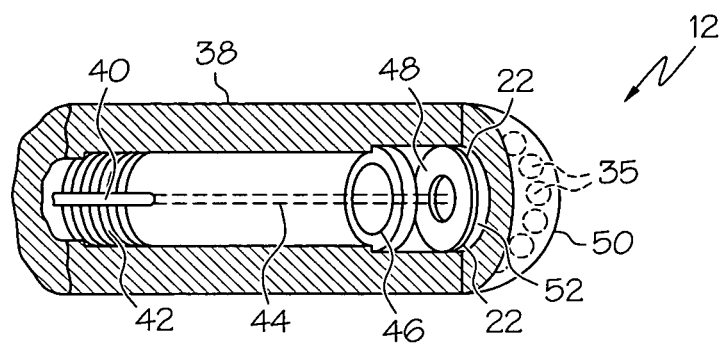
FIG. 4 is a diagrammatic, section view of the scanned beam imaging unit of FIG. 3.

Referring now to FIG. 3, scanned beam imaging unit 12 includes a housing 38 that encloses and supports the reflector 22. An optical fiber 40 (e.g., a single mode optical fiber) is used to deliver light (e.g., one or more imaging laser beams at various visible wavelengths such as red, green and blue) from the light source 18 to the scanned beam imaging unit 12. Referring also to FIG. 4, the optical fiber 40 is affixed to the housing 38 using a ferrule 42. The end of the optical fiber 40 may be polished to create a known divergence angle of raw beam 44. Raw beam 44 is shaped by a beam shaping optic or lens 46 to create a beam shape appropriate for transmission through the system. After shaping, shaped beam 48 is fed through an aperture in the center of reflector 22, reflected off a first reflecting surface 52 back onto the front of the reflector and then out of the scanned beam imaging unit 12, the details of which are described in U.S. patent application Ser. No. 10/873,540, already incorporated by reference above.

Scanned beam imaging unit 12 may further include a dome 50. The dome 50 includes the reflecting surface 52 and the inside and/or outside of the dome may have optical power and further shape the beam as it passes therethrough. In some embodiments, dome 50 provides a hermetic seal with the housing 38 to protect the optical elements from the environment.

Control and/or power leads 54 (shown in FIG. 3) pass through the ferrule 42 and connect to the reflector 22, providing a drive signal and optionally position feedback. Leads 54 may also provide control and feedback connections for controlling focus characteristics of the beam shaping optic 46.

Light collecting fibers 35 (shown in FIG. 4 by dotted lines) are enclosed by the housing 38 and dome 50. Light collecting fibers 35 may be multi-mode optical fibers that transmit the light to the detectors 34 in control unit 14 (see FIG. 1) or, in some embodiments, the light collecting fibers 35 may be replaced by optical-to-electrical converters such as photodiodes.

Figure 5:
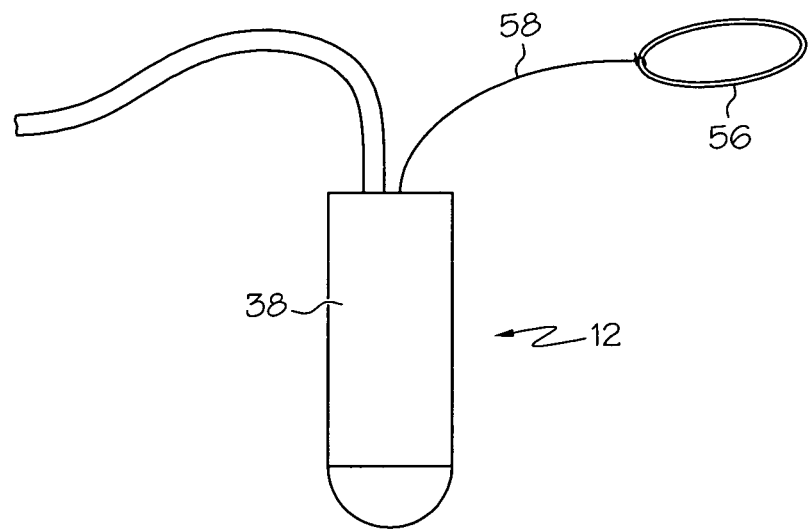
FIG. 5 is a side view of an embodiment of a scanned beam imaging unit including connecting structure.

Referring to FIG. 5, the scanned beam imaging unit 12 may include anatomy connecting structure, in this case suture loop 56, for affixing the scanned beam imaging unit at an imaging location within the anatomy. The suture loop 56 is attached to the housing 38 by a tether 58 (e.g., formed of an absorbable or non-absorbable material). The tether 58 may be formed of any suitable material such as a polymeric material.

Figure 6:
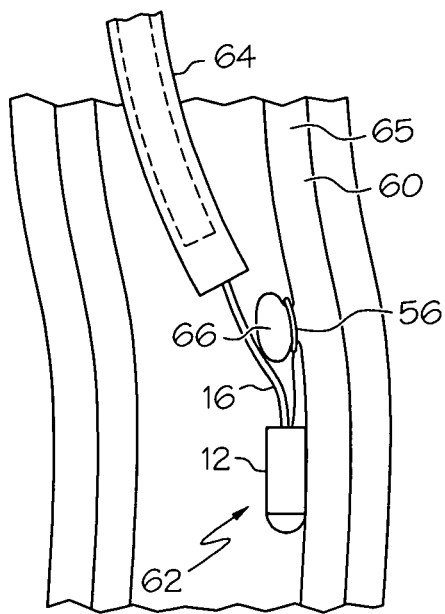
FIG. 6 illustrates a system and method of connecting the scanned beam imaging unit of FIG. 5 within a lumen.

FIG. 6 shows the scanned beam imaging unit 12 connected to a lumen wall 60 within a patient's body using the suture loop 56 to position the scanned beam imaging unit at an imaging location 62. A locating instrument 64 (e.g., an endoscope) can be used to locate the scanned beam imaging unit 12 at the imaging location 62 and also to place the suture loop 56 about a protuberance 66 formed by the lumen wall 60. The line 16 (e.g., including the optical fiber 40 and leads 54) extends through the lumen 65 and channel of the locating instrument 64, for example, back to the control unit 14 (see FIG. 1).

Figure 7:
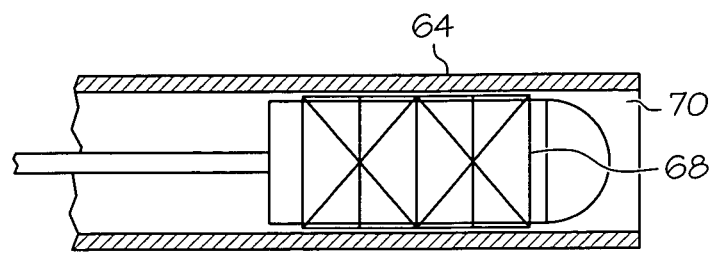
FIG. 7 illustrates another embodiment of a scanned beam imaging unit including connecting structure located within a channel of a locating device for delivery to an imaging location.
Figure 8:
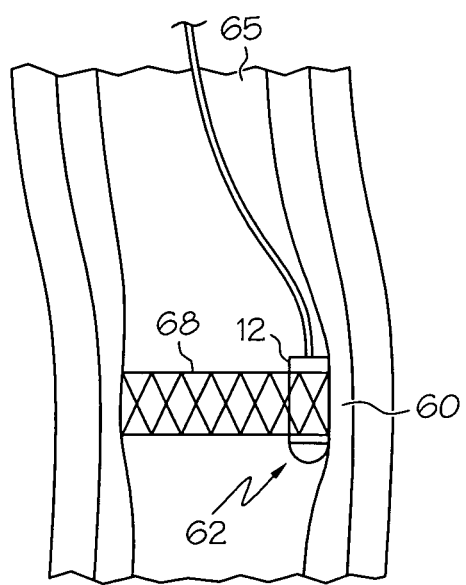
FIG. 8 illustrates the scanned beam imaging unit of FIG. 7 located within a lumen at an imaging location.

In another embodiment shown by FIGS. 7 and 8, the scanned beam imaging unit 12 includes stent-like, expandable connecting structure 68 (e.g., e.g., formed of metal, silicone or a hybrid material) for anchoring the scanned beam imaging unit in the lumen 60. FIG. 7 shows the connecting structure 68 in a collapsed configuration inside the channel 70 of the locating instrument 64 for delivery to the imaging location 62. Referring to FIG. 8, once the scanned beam imaging unit 12 is located at the imaging location 62, the scanned beam imaging unit may be removed from the channel 70 allowing the connecting structure 68 to expand into contact with the lumen wall 60 as shown. In some embodiments, as shown, the scanned beam imaging unit 12 is located near to the lumen wall 60 so as to place the scanned beam imaging unit away from the center of the lumen 65 to facilitate passage of fluid thereby. The connecting structure 68 may be selfexpanding (e.g., outwardly biased or formed of a memory shape material) or may be dilated, for example, using a balloon.

Figure 9:
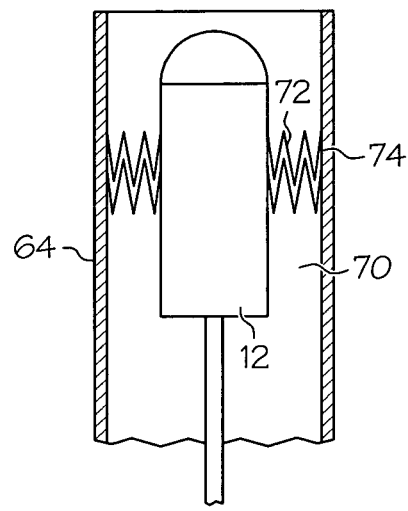
FIG. 9 illustrates another embodiment of a scanned beam imaging unit including connecting structure located within a channel of a locating device for delivery to an imaging location.
Figure 10:
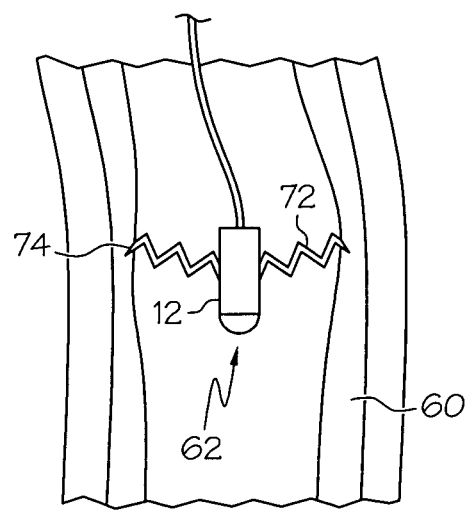
FIG. 10 illustrates the scanned beam imaging unit of FIG. 9 located within a lumen at an imaging location.

FIGS. 9 and 10 illustrate another scanned beam imaging unit 12 including expandable connecting structure 72 with barbs 74 for use in anchoring the scanned beam imaging unit to the lumen wall 60. FIG. 9 shows the connecting structure 72 in a collapsed configuration inside the channel 70 of the locating instrument 64 for delivery to the imaging location 62. Referring to FIG. 10, once the scanned beam imaging unit 12 is located at the imaging location 62, the scanned beam imaging unit may be removed from the channel 70 allowing the connecting structure 72 to expand into contact with the lumen wall 60 as shown with the barbs 74 penetrating the lumen wall 68 to anchor the scanned beam imaging unit thereto.

Other securing features for fixing the scanned beam imaging unit 12 at an imaging location within the anatomy for a period of time include a magnet, a clamp, an adhesive material, etc. In some instances, the scanned beam imaging unit 12 may be located at the imaging location using the anatomy itself without any need for connecting structure or material. In some embodiments, the scanned beam imaging unit 12 may be attached to other structure inserted into the anatomy at a fixed location such as a trocar where the other structure has its own functionality.

Figure 11:
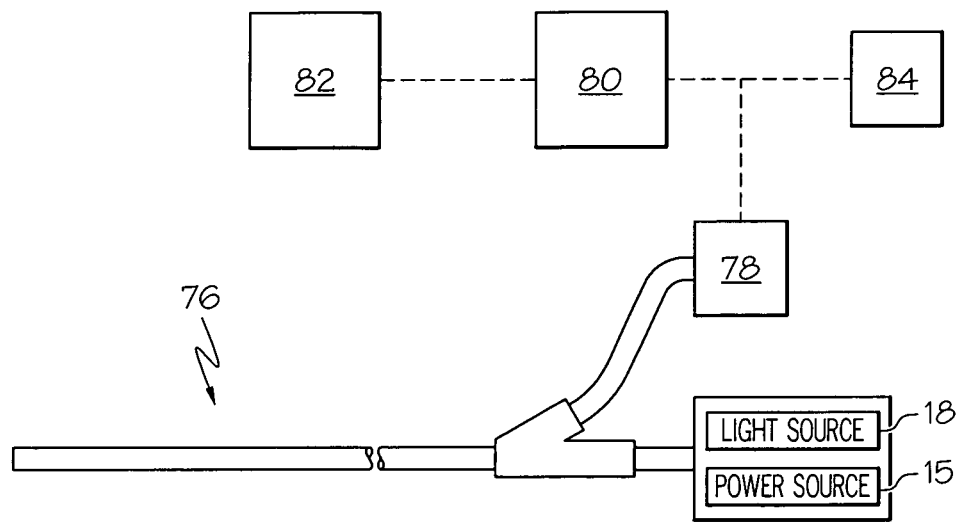
FIG. 11 is a somewhat diagrammatic view of a locating instrument including a scanned beam imaging unit.
Figure 12:
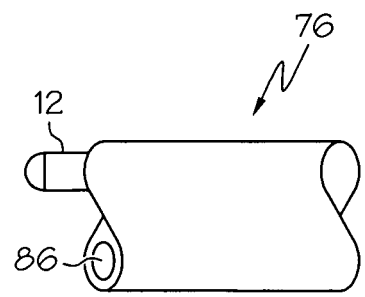
FIG. 12 is a partial, section view of the locating instrument of FIG. 11 showing the scanned beam imaging unit.

Referring now to FIGS. 11 and 12, in some embodiments, the scanned beam imaging unit 12 (FIG. 12) may be used to provide an image of the anatomy while being delivered to the imaging location using the locating instrument 76 (FIG. 11). Light reflected from the portion of the anatomy is gathered and returned through the locating instrument 76 to a photo detector 78 which generates electronic signals that are proportional to the intensity of the received light. The electronic signals may be supplied to an image processor 80 that combines the electronic signals and creates an image for display by display device 82. The images may be recorded and stored in a database 84 for recall by the image processor 82. Once the scanned beam imaging unit 12 reaches the desired imaging location within the anatomy, the scanned beam imaging unit may be fixed at the imaging location for a period of time and, in some embodiments, connected to the control unit 14. The locating instrument 76 may further include one or more working channels 86 for the passage of surgical instruments in order for a surgeon to perform various surgical procedures.

Figure 13:
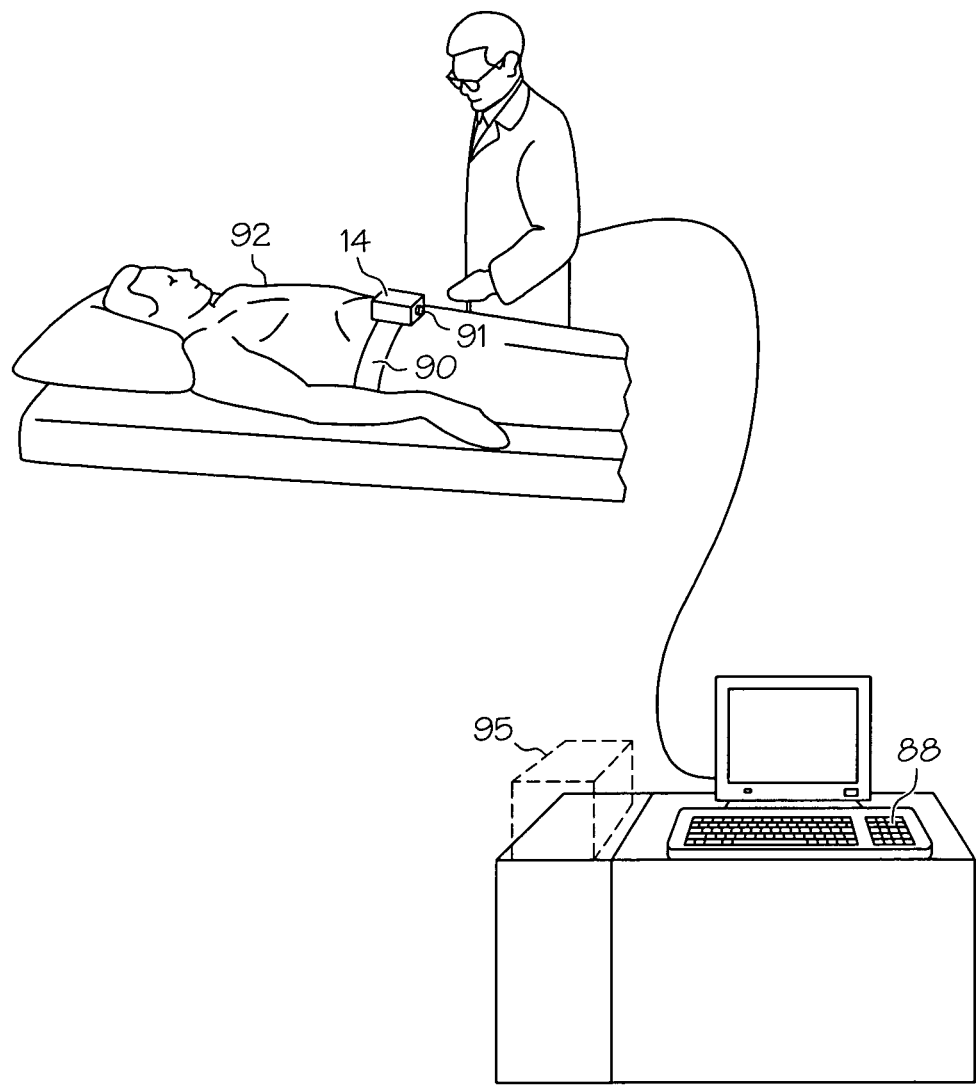
FIG. 13 illustrates an exemplary system and method of monitoring a condition within a patient's body using the imaging system of FIG. 1.

Referring to FIG. 13, in some embodiments, control unit 14 may be portable and record and store image data generated using the scanned beam imaging unit 12 for later processing and viewing. As used herein, the term "portable" refers to the capability of being transported during use. In the illustrated example, the control unit 14 includes a connection or port 91 for connecting an image processor 88 (e.g., a computer) to the control unit so that the image processor can obtain the image data therefrom. In some embodiments, the control unit 14 may be wirelessly linked to the image processor 88. The control unit 14 may be wearable, for example, using a belt 90 connected thereto and positioned about the waist of the patient 92. This can allow for image data collection while the patient 92 is away from the image processing site, e.g., the hospital, clinic, etc. Any other suitable wearable or carriable support structure for the mobile control unit may be used, such as a pouch, bag, pocket, pack, etc.

In some embodiments, the patient 92 may deliver the portable control unit 14 and/or the image data contained therein to the image processing site (e.g., by courier, network connection, etc.) after which the image data is obtained from the mobile control unit outside the presence of the patient at the image processing site. In a post-processing step, the stored image data may be downloaded from the mobile control unit 14 (e.g., via the Internet, through a wired or wireless connection, etc.) to the image processor for post-processed reconstruction of the video image. In some embodiments, the image processor 88 may include a docking station 95 (shown by dotted lines) that is used to facilitate data transfer (image data and/or otherwise) from the mobile control unit 14. Advantageously, this can allow for image data processing and viewing without the patient' presence at the image processing site. In some embodiments, the mobile control unit 14 may have a memory capacity to record image data for only a selected period of time such as 24 hours, 36 hours, 48 hours, etc.

Figure 14:
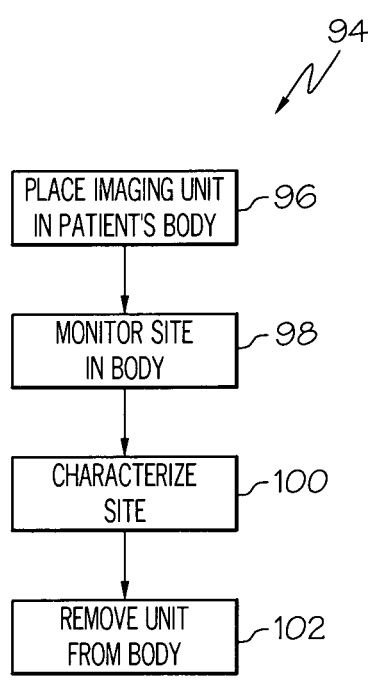
FIG. 14 illustrates an embodiment of a method of using an imaging system.

In some embodiments, the imaging system 10 may be used to monitor the efficacy of a certain procedure after performing therapy and/or to diagnose a behavior of a structure prior to therapy. Referring to FIG. 14, a method 94 of monitoring a site within a patient's body includes, at step 96, placing a scanned beam imaging unit 12 within the anatomy (e.g., using a locating instrument, or percutaneously using a needle or some other introducing instrument). At step 98, the site within the patient's body is monitored over time (e.g., 2 hours, 6 hours, 12 hours, 24 hours, 48 hours, etc.) using image data generated by the imaging system 10, for example, with the locating instrument removed from the patient's body. Once the behavior is characterized or after a pre-selected period of time has passed at step 100, the scanned beam imaging unit 12 is removed from the anatomy by any suitable method at step 102. Suitable methods include use of a steerable instrument, passing the scanned beam imaging unit out any natural orifice (e.g., mouth, anus, nose, etc.), passing the scanned beam imaging unit through a drain tube (e.g., through the abdomen or other opening), cutting the lines 50 and 54 and allow the scanned beam imaging unit to pass naturally, cutting the lines and removing the scanned beam imaging unit percutaneously using a cannula or needle, etc.

In one example, a scanned beam imaging unit 12 of an imaging system 10 may be located in the esophagus along with an esophageal pH monitor (see pH monitor element 104 in FIG. 1). Data may be collected from both the imaging system 10 and pH monitor over a period of time such as 24 hours. An exemplary pH monitoring system is a Bravo Wireless Esophageal pH Monitoring System, commercially available from Medtronic, Inc. Both the scanned beam imaging unit 12 and the pH monitor may be removed once the 24 hour time period has lapsed. Data from the imaging system 10 and the pH monitor may be correlated (e.g., using timestamps), which can provide the advantage of gathering both physical data in correlation with pH (or other types) of data. In some embodiments, control unit 14 is used to collect and record both the image and pH data.

Figure 15:
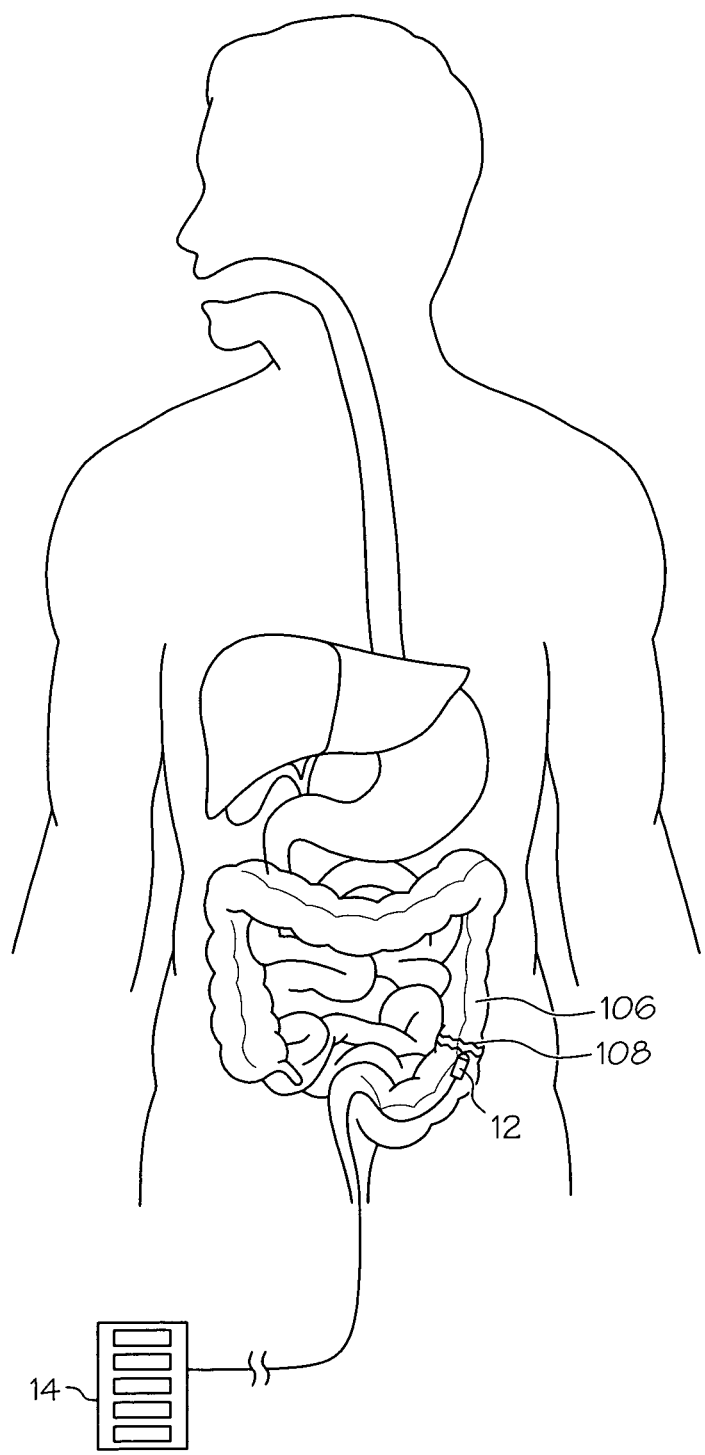
FIG. 15 illustrates a scanned beam imaging unit being used to monitor a lower gastrointestinal tract of a patient.
Figure 16:
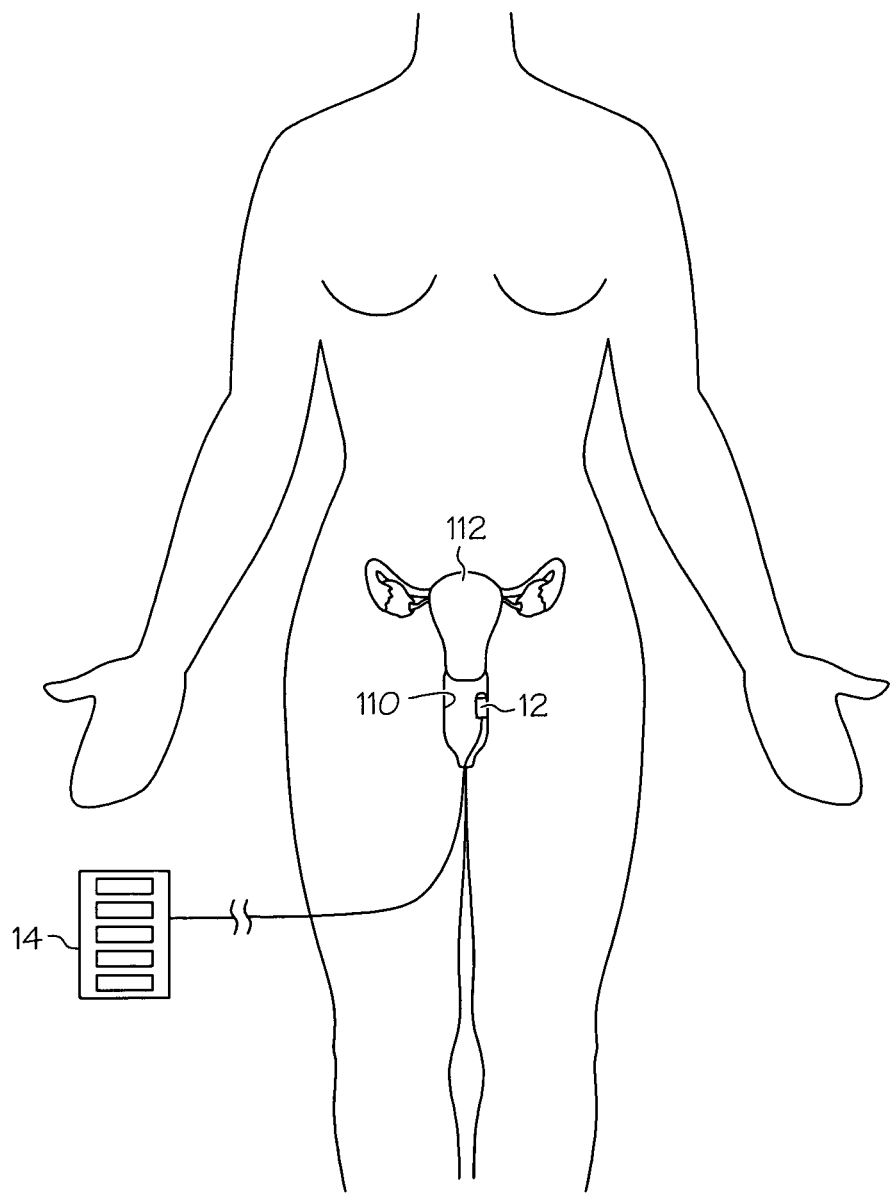
FIG. 16 illustrates a scanned beam imaging unit being used to monitor gynecological conditions, fertility or pregnancy events within a patient.
Figure 17:
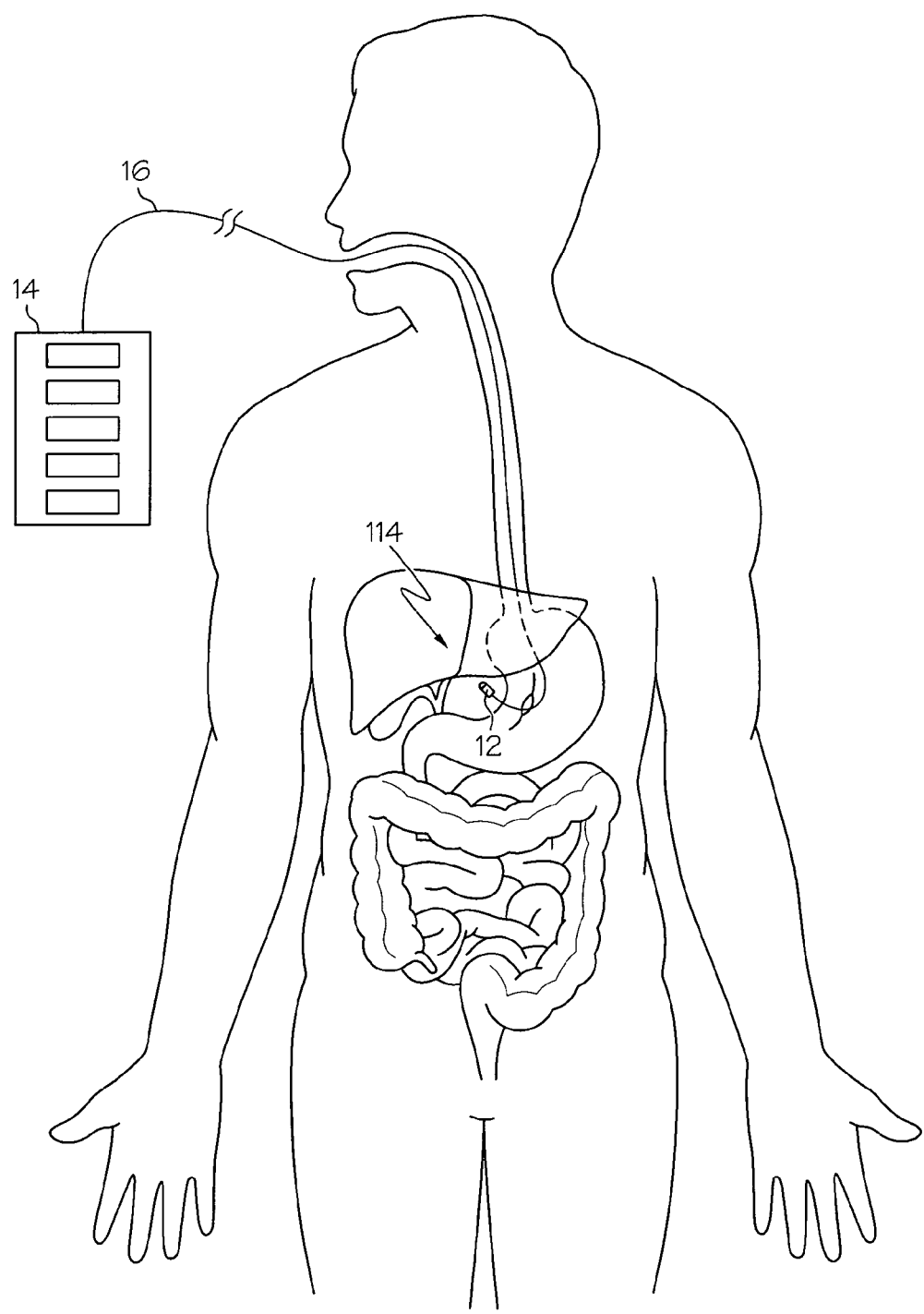
FIG. 17 illustrates a scanned beam imaging unit being used to monitor a peritoneal cavity of a patient.

FIGS. 15-17 illustrate placement of the scanned beam imaging unit 12 at certain locations to monitor various parts of the anatomy. Referring to FIG. 15, the scanned beam imaging unit 12 is located to monitor a portion of the gastrointestinal tract 106. The imaging unit 12 may be fixedly located within the gastrointestinal tract 106 at an imaging location using connecting structure 108 (e.g., one or more of the connecting structures described above) for a desired period of time. As described above, control unit 14 may be connected to the scanned beam imaging unit 12 for use in generating an image of the portion of the gastrointestinal tract 106. FIG. 16 demonstrates the use of the scanned beam imaging unit 12 to monitor gynecological conditions, fertility or pregnancy events. The scanned beam imaging unit 12 may be affixed to a wall 110 of the uterus 112 of the patient to view an image of a desired portion of the anatomy. Referring to FIG.

17, the scanned beam imaging unit 12 is utilized to monitor the peritoneal cavity 114 of the patient.

The above described imaging system 10 allows for placement of the scanned beam imaging unit 12 at a fixed imaging location with the anatomy where the scanned beam imaging unit can be used to monitor a certain portion of the anatomy over a period of time (e.g., for a selected period of time and/or until the condition is characterized or recovery from a surgical procedure is complete). A continuous stream of imaging data can be generated by the imaging system 10 and saved in memory of a control unit 14 to be processed and displayed as a video image (e.g., using a SVGA display). The control unit 14 is located outside the patient's body and may include the light source, detector, power source and memory for storing image data. In some embodiments, the image data may be generated and stored within a mobile control unit 14 that is connected to or carried by the patient removed from the imaging processing location which can provide the patient with some freedom to move from place to place (e.g., at home) while the image data is being collected for later processing.

It should be noted that while the scanned beam imaging unit 12 is often shown connected to the control unit 14 by line 16. The line 16 may be releasably connected to the control unit 14. That is, the control unit 14 may be disconnected from the line 16 and scanned beam imaging unit 12 with the scanned beam imaging unit located at the imaging location within the patient's body. The control unit 14 may be connected to the line 16 (e.g., using a port) when it is desired to view the desired portion of the anatomy. This connect and disconnect feature may be desirable, for example, to monitor a gastroplasty so that a doctor can monitor conditions from time-to-time. In these embodiments, control unit 14 may not be wearable and may include both data storage and video generating features.

A number of detailed embodiments have been described. Nevertheless, it will be understood that various modifications may be made. Accordingly, other embodiments are within the scope of the following claims.

What is claimed is:

1. A method of monitoring a condition within a patient's body, the method comprising:
    locating a scanned beam imaging unit at an imaging location by connecting structure between the scanned beam imaging unit and an anatomical structure for a period of time to observe and characterize a portion of the patient's anatomy over at least a portion of the period of time, the connecting structure selected from the group consisting of a suture loop, an expandable stent, a barbed anchor, or a clamp, the scanned beam imaging unit being located at the imaging location using a locating instrument;
    removing the locating instrument from the patient's body with the scanned beam imaging unit remaining at the imaging location;
    providing a control unit including a detector, a memory, and a light source for creating a beam of light, the control unit driving the scanned beam imaging unit from outside of the patient's body via a line connecting the control unit to the scanned beam imaging unit; and
    with the scanned beam imaging unit at the imaging location:
        scanning the beam of light across the portion of the anatomy; and
        receiving light from the portion of the anatomy;
    and with the control unit outside of the patient's body:
        detecting the received light using the detector;
        producing imaging data from the detected received light; and
        saving the imaging data in the memory;
    then, after saving the imaging data in the memory, connecting the control unit to an image processor for processing the imaging data, the image processor producing a video image of the portion of the anatomy from the imaging data.

2. The method of claim 1 further comprising producing continuous imaging data from the detected light using the detector.

3. The method of claim 1 wherein the line connecting the control unit to the scanned beam imaging unit is a disconnectable and reconnectable line.

4. The method of claim 1 further comprising carrying the control unit while imaging data is being produced, the control unit being carried by the patient as the patient moves from place to place.

5. The method of claim 1 further comprising removing the scanned beam imaging unit from the imaging location after the period of time.

6. The method of claim 5 further comprising disconnecting the connecting structure affixing the scanned beam imaging unit at the imaging location to remove the scanned beam imaging unit from the imaging location.

7. The method of claim 1 further comprising locating a monitoring device within the patient's body, the monitoring device generating data indicative of a condition within the patient's body other than imaging data.

8. The method of claim 7 further comprising timestamping the imaging data, timestamping the data generated by the monitoring device, and correlating the data generated by the monitoring device and the imaging data using the respective timestamps.

9. The method of claim 1 wherein the connecting structure consists of a suture loop, the suture loop having a first end connected to the scanned beam imaging unit and a second end connectable to a protuberance formed by the portion of the patient's anatomy.

10. The method of claim 1 wherein the portion of the patient's anatomy comprises a lumen.

11. The method of claim 10 wherein the connecting structure consists of an expandable stent.

12. The method of claim 11 wherein the scanned beam imaging unit is attached to the stent so as to locate the scanned beam imaging unit away from the center of the lumen to facilitate passage of fluid thereby.

13. The method of claim 12 wherein the stent comprises a metal, silicone, or hybrid material.

14. An imaging system for monitoring a condition within a patient's body, the imaging system comprising:
    a scanned beam imaging unit comprising a reflector that directs a beam of light across a portion of the patient's anatomy;
    a portable control unit driving the scanned beam imaging unit, the portable control unit comprising a power source, a light source that generates the beam of light a memory for saving imaging data generated using the scanned beam imaging unit, and a data processor configured to transmit the imaging data from the memory to an image processor; and
    connecting structure that attaches the scanned beam imaging unit to an anatomical structure at an imaging location within the patient's body;
    wherein the scanned beam imaging unit is configured to be placed in the patient's body with said connecting structure selected from the group consisting of a suture loop, an expandable stent, a barbed anchor; and a clamp, and wherein the portable control unit is configured to be located outside the patient's body and, after the imaging data is saved in the memory, subsequently connected to the image processor to generate a video image of the portion of the patient's anatomy.

15. The imaging system of claim 14 further comprising an optical fiber connecting the control unit and the scanned beam imaging system, the optical fiber directing the beam of light from the portable control unit to the scanned beam imaging unit.

16. The imaging system of claim 14, wherein the scanned beam imaging unit further comprises a detection optical fiber that receives light from the portion of the patient's anatomy and transmits received light to the portable control unit.

17. The imaging system of claim 16, wherein the portable control unit further comprises a detector that receives the light from the detection optical fiber and generates the imaging data.

18. The system of claim 14 wherein the connecting structure consists of a suture loop, the suture loop having a first end connected to the scanned beam imaging unit and a second end connectable to the anatomical structure.

19. The system of claim 14 wherein the condition within a patient's body is located within a body lumen.

20. The system of claim 19 wherein the scanned beam imaging unit is attached to the expandable stent so as to locate the scanned beam imaging unit away from the center of the lumen to facilitate passage of fluid thereby.

21. A method of monitoring a condition within a patient's body, the method comprising:
connecting a scanned beam imaging unit by a connecting structure to an anatomical structure within the patient's body at an imaging location for a period of time to observe and characterize a portion of the patient's anatomy over at least a portion of the period of time;
providing a portable control unit in communication with the scanned beam imaging unit with the scanned beam imaging unit located at the imaging location, the portable control unit driving the scanned beam imaging unit and including a recording medium for saving imaging data generated using the scanned beam imaging unit for producing a video image of the portion of the patient's anatomy;
saving imaging data generated using the scanned beam imaging unit on the recording medium; and
after saving the imaging data, connecting the portable control unit to an image processor for processing the imaging data and producing the video image of the portion of the patient's anatomy;
wherein said connecting structure is selected from the group consisting of a suture loop, an expandable stent, a barbed anchor, and a clamp.

22. The method of claim 21 further comprising connecting the portable control unit to the scanned beam imaging unit by a line including an optical fiber for directing a beam of light from the portable control unit to the scanned beam imaging unit, wherein the portable control unit is located outside the patient's body.

23. The method of claim 21 wherein the connecting structure consists of a suture loop, the suture loop having a first end connected to the scanned beam imaging unit and a second end connectable to a protuberance formed by the anatomical structure.

24. The method of claim 21 wherein the condition of the patient's body is located at a body lumen.

25. The method of claim 24 wherein the connecting structure consists of an expandable stent.

26. The method of claim 25 wherein the scanned beam imaging unit is attached to the stent so as to locate the scanned beam imaging unit away from the center of the lumen to facilitate passage of fluid thereby.

27. The method of claim 26 wherein the stent comprises a metal, silicone, or hybrid material.

* * * * *